United States Patent [19]

Tornier

[11] 4,287,617
[45] Sep. 8, 1981

[54] FEMORAL PIN FOR HIP PROSTHESIS

[75] Inventor: Alain Tornier, Le Brocey-Crolles, France

[73] Assignee: Etablissements Tornier, Saint Ismier, France

[21] Appl. No.: 81,229

[22] Filed: Oct. 2, 1979

[30] Foreign Application Priority Data

Oct. 11, 1978 [FR] France .................. 78 29595

[51] Int. Cl.³ .............................................. A61F 1/03
[52] U.S. Cl. .................. 3/1.913; 128/92 BC; 128/92 CA
[58] Field of Search ........... 128/92 BC, 92 CA, 92 C; 3/1.913, 1.912

[56] References Cited

U.S. PATENT DOCUMENTS

| 3,466,670 | 9/1969 | Christiansen | 128/92 CA X |
| 3,848,273 | 11/1974 | Frey | 3/1.913 |
| 3,893,196 | 7/1975 | Hochman | 128/92 BC X |

FOREIGN PATENT DOCUMENTS 913228 6/1954 Fed. Rep. of Germany ... 128/92 BC

OTHER PUBLICATIONS

"Intramedullary Nails", Zimmer Product Encyclopedia, pp. B53–B56, Jun. 1978.
Charnley, "Intramedullary Nailing of Fractures", Journal of Bone and Joint Surgery, p. 162, Oct. 5, 1951.

Primary Examiner—Clifford D. Crowder
Attorney, Agent, or Firm—Dowell & Dowell

[57] ABSTRACT

A hip prosthesis of which the pin is made in the form of a tube slit in the longitudinal direction in order to give it a transverse elasticity and means enabling the bone to regrow inside this pin. Said pin further comprises a crest or fin provided with openings.

4 Claims, 3 Drawing Figures

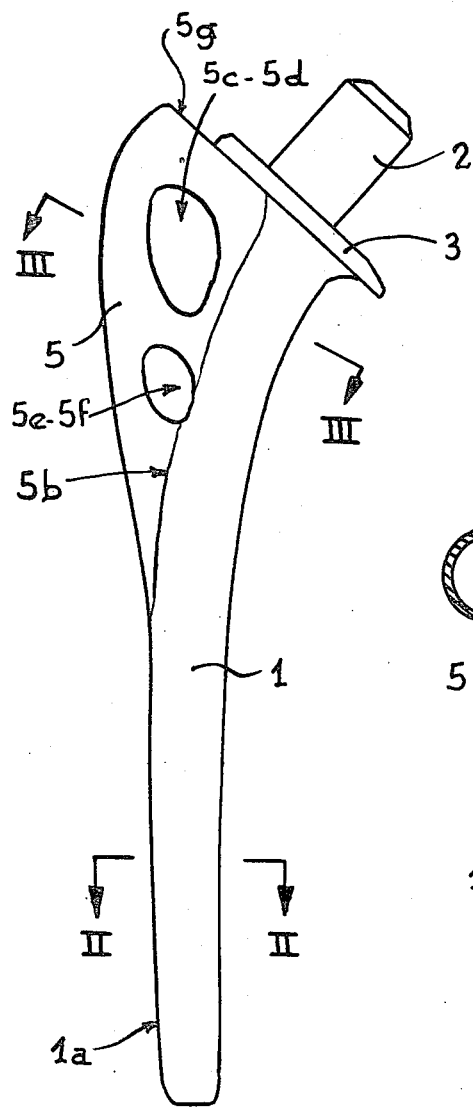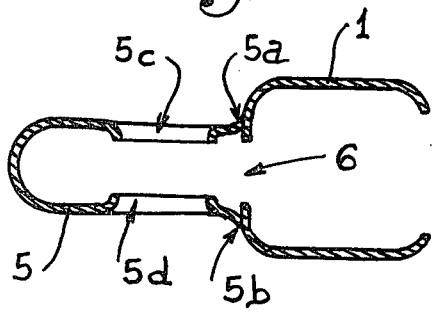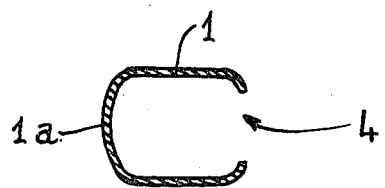

FEMORAL PIN FOR HIP PROSTHESIS

The present invention relates to improvements in prostheses for the hip of the type comprising a femoral pin which is driven into the medullary cavity of the femur and the end of which bears a ball joint adapted to be engaged in the natural or artificial acetabulum of the hip bone.

The femoral pins of known prostheses are rigid, with the result that it is relatively difficult for them to abut suitably on the cortices. Due to the considerable stresses that they absorb, their upper part may develop clearance with the bone, this bringing about shearing movements even if the prosthesis is cemented in. In addition, they are heavy, as they are solid.

It is an object of the improvements according to the present invention to remedy these drawbacks and to provide a prosthesis of which the femoral pin has a transverse elasticity which enables it to abut as well as possible against the cortices of the femur.

The pin of the prosthesis according to the invention is made in the form of a tube slit in the longitudinal direction, one of the ends of which is fixed to a hilt member provided in known manner and supporting a pivot on which the ball joint is journalled, and wherein said pin presents elasticity in the transverse direction in order to ensure an excellent abutment of its periphery against the cortices of the femur.

The invention will be more readily understood on reading the following description with reference to the accompanying drawings, in which:

FIG. 1 is a view in elevation of the femoral pin of a prosthesis according to the invention.

FIGS. 2 and 3 are sections thereof, on a larger scale, along II—II and III—III (FIG. 1) respectively.

Referring now to the drawings, FIG. 1 shows the femoral pin of a hip prosthesis according to the invention, comprising a pin 1 surmounted by a pivot 2 which extends perpendicularly with respect to a hilt member 3, as is well known in the art.

According to the invention, the pin 1 is, in transverse section in the form of a substantially rectangular tube of which a first one of the small sides is virtually cut away so as to leave a very large slot 4 (FIG. 2). It is observed that the second small side 1a of the pin 1 is curvilinear. A C-shaped section is thus obtained which exhibits excellent transverse elasticity, this facilitating the positioning of the pin in the medullary cavity by insertion. Of course, the section shown in FIG. 2 could take another form, and in particular it could take the exact internal shape of this cavity. Other considerable advantages of such a pin are that it is not heavy and it enables the bone which is regrowing after the prosthesis has been placed in position, to fill in all the hollow parts thereof. This is obviously an important factor in achieving solid coupling.

The outer and lower faces of the pin 1 may be made rough in order to facilitate its anchoring with respect to the cortices. They could also comprise a surface with cavities as described in French Pat. No. 72 27966.

It is known that prior art solid femoral pins of hip prostheses sometimes include a crest or fin ensuring the maintenance of its orientation with respect to the femur. The prosthesis according to the invention may include a crest or fin of this type, generally designated under reference 5 and made in the form of a U-shaped curved sheet metal blank, whose edges are welded to the pin 1 along lines 5a, 5b (FIGS. 1 and 3). Of course, the convex side 1a of the pin 1 is cut out longitudinally to form a slot 6 at right angles to the crest 5. The crest includes on its side faces corresponding openings 5c–5d, 5e–5f through which the bone regrows and fills in the interior of the crest.

It will be noted that the end 5g of the crest is closed by a transverse partition located at the level of the lower face of the hilt member 3.

A femoral pin for a hip prosthesis has thus been produced which is particularly well adapted to the medullary cavity and which allows the possibility of considerable bone growth. Of course, such a prosthesis may be fixed to the medullary cavity by means of a conventional plastic seal which reinforces the anchoring effect ensured by the above-mentioned bone growth.

The description given hereinabove has, of course, been given only by way of example and it in no way limits the field of the invention, the replacement of details described by any other equivalents not departing from the scope thereof.

What is claimed is:

1. In a hip prosthesis of the type having a hilt member for engaging the end of a femur and having a pivot member extending from the hilt member in one direction and having a pin member extending longitudinally from the hilt member in the other direction and the pin member having a contour curved as viewed in a plane parallel to its longitudinal axis and shaped to fit into the medullary cavity of the femur, the improvement wherein the pin member comprises:
    (a) a generally C-shaped member having two opposed similar curved sides lying parallel to said plane, and having first and second sides disposed generally at right angles to said plane, the first side being open to provide a slot extending longitudinally from the hilt member to provide the pin with elasticity transversely of said plane; and
    (b) a crest member which is U-shaped in cross section and extends partway along the second side of the C-shaped member from the hilt member and has its free edges joined to the second side of the C-shaped member, said second side of the C-shaped member having a shorter longitudinal slot between said free edges opposite the slot in the first side.

2. The hip prosthesis as claimed in claim 1, wherein the crest member has a pattern of openings therethrough to receive bone growth.

3. The hip prosthesis as claimed in claim 1, wherein the pin member comprises a curved metal tube wherein said longitudinal slot extends full length on its first side and the shorter longitudinal slot extending part-way along its second side.

4. The hip prosthesis as claimed in claim 3, wherein the crest member comprises a U-shaped metal member abutting the hilt member and having its free edges welded to said tube adjacent to said shorter slot, the crest member tapering into the contour of the second side of the pin member at the end of the shorter slot.

* * * * *